US011495205B2

(12) United States Patent
Zafeiropoulos et al.

(10) Patent No.: US 11,495,205 B2
(45) Date of Patent: Nov. 8, 2022

(54) SILENT ZONE GENERATION

(71) Applicant: Harman Becker Automotive Systems GmbH, Karlsbad (DE)

(72) Inventors: Nikos Zafeiropoulos, Straubing (DE); Koukias Stamatios, Stuttgart (DE)

(73) Assignee: Harman Becker Automotive Systems GmbH, Karlsbad (DE)

( * ) Notice: Subject to any disclaimer, the term of this patent is extended or adjusted under 35 U.S.C. 154(b) by 0 days.

(21) Appl. No.: 17/273,233

(22) PCT Filed: Sep. 13, 2018

(86) PCT No.: PCT/EP2018/074686
§ 371 (c)(1),
(2) Date: Mar. 3, 2021

(87) PCT Pub. No.: WO2020/052759
PCT Pub. Date: Mar. 19, 2020

(65) Prior Publication Data

US 2022/0108679 A1 Apr. 7, 2022

(51) Int. Cl.
*A61F 11/06* (2006.01)
*G10K 11/178* (2006.01)
(Continued)

(52) U.S. Cl.
CPC .. *G10K 11/17815* (2018.01); *G10K 11/17857* (2018.01); *G10K 11/17875* (2018.01);
(Continued)

(58) Field of Classification Search
CPC ....... G10K 11/17815; G10K 11/17857; G10K 11/17875; G10K 2210/1282; H04R 1/406; H04R 3/005; H04R 2410/05
(Continued)

(56) References Cited

U.S. PATENT DOCUMENTS 5,602,928 A * 2/1997 Eriksson .......... G10K 11/17885 381/71.7
2016/0100250 A1* 4/2016 Baskin ..................... H04R 1/02 297/217.4
2018/0190259 A1 7/2018 Woelfl et al.

FOREIGN PATENT DOCUMENTS

EP 0721178 A2 7/1996
EP 2884488 A1 6/2015
(Continued)

OTHER PUBLICATIONS

International Search Report dated Jun. 6, 2019 for PCT Appn. No. PCT/EP2018/074686 filed Sep. 13, 2018, 14 pgs.
(Continued)

*Primary Examiner* — Ammar T Hamid
(74) *Attorney, Agent, or Firm* — Brooks Kushman P.C.

(57) ABSTRACT

A system for generating silent zones at a listening position comprises a first loudspeaker disposed at a first position and configured to radiate sound that corresponds to a sound signal. A first microphone picks up noise radiated by a noise source to the listening position and generates a first microphone signal. A second loudspeaker disposed at a second position that radiates sound. A second microphone that generates a second microphone signal. A third microphone disposed at a third position that generates a third microphone signal. An active noise cancellation (ANC) controller that receives the third microphone signal and at least one of the first and second microphone signals and that provides a loudspeaker input signal. A distance between the third position and the first position equals a distance between the third position and the second position such that the first, second and third microphones form corners of an isosceles triangle.

23 Claims, 7 Drawing Sheets

(51) Int. Cl.
*H04R 1/40* (2006.01)
*H04R 3/00* (2006.01)
*G10K 11/16* (2006.01)

(52) U.S. Cl.
CPC ............. *H04R 1/406* (2013.01); *H04R 3/005* (2013.01); *G10K 2210/1282* (2013.01); *H04R 2410/05* (2013.01)

(58) Field of Classification Search
USPC .......................................................... 381/71.4
See application file for complete search history.

(56) References Cited

FOREIGN PATENT DOCUMENTS

| | | | | | |
|---|---|---|---|---|---|
| EP | 3001416 | A1 | | 3/2016 | |
| JP | H0561479 | A | | 3/1993 | |
| JP | H0659683 | A | | 3/1994 | |
| JP | H06161466 | A | | 6/1994 | |
| JP | 2007003994 | A | | 1/2007 | |
| WO | WO-2009129008 | A1 | * | 10/2009 | ............. H04R 3/005 |
| WO | 2016210050 | A1 | | 12/2016 | |
| WO | WO-2016210050 | A1 | * | 12/2016 | ....... G10K 11/17823 |

OTHER PUBLICATIONS

English Translation of Japanese Office Action dated Aug. 25, 2022 for Japanese Application No. 2021-506415 filed Feb. 5, 2021, 6 pgs.

* cited by examiner

SILENT ZONE GENERATION

CROSS-REFERENCE TO RELATED APPLICATION

This application is the U.S. national phase of PCT Application No. PCT/EP2018/074686 filed on Sep. 13, 2018, the disclosure of which is incorporated in its entirety by reference herein.

BACKGROUND

1. Field

The disclosure relates to systems and methods (generally referred to as "systems") for the generation of a silent zone.

2. Related Art

Active noise cancellation systems generally reduce the sound pressure level in a defined silent zone at least for a certain frequency range. In a vehicle, loudspeakers and error microphones of an active noise cancellation system are arranged at defined positions within the vehicle. Therefore, a silent zone is generated at a fixed active noise cancellation (ANC) position with respect to the positions of the loudspeakers and microphones. Usually, one separate silent zone is generated for each ear of the user. A user perceives the system as working satisfactory, if each of the user's ears is located within one of the silent zones. However, if the user moves his/her head such that his/her ears are subsequently located outside the silent zones, the user experiences a less satisfactory noise cancellation experience. Further, the silent zones are usually arranged at positions such that a standard user's ears will be located within the silent zone when the user looks straight ahead. However, users that have an "out of the norm" anatomy may experience less satisfactory results, as their ears might not be fully located in the silent zones, even when taking on a preferential position.

SUMMARY

A system for generating silent zones at a listening position comprises a first loudspeaker disposed at a first position adjacent to the listening position and configured to radiate sound that corresponds to a sound signal, a first error microphone disposed at the first position and configured to pick up noise radiated by a noise source via a primary path to the listening position. The first loudspeaker is configured to generate a corresponding first microphone signal, a second loudspeaker disposed at a second position adjacent to the listening position and configured to radiate sound that corresponds to a sound signal, a second error microphone disposed at the second position and configured to pick up noise radiated by a noise source via a primary path to the listening position and configured to generate a corresponding second microphone signal, a third microphone disposed at a third position adjacent to the listening position and configured to pick up noise radiated by a noise source via a primary path to the listening position and configured to generate corresponding third microphone signals. An ANC controller is configured to receive the microphone signals from the third microphone and at least one of the first and second microphone, and to provide a loudspeaker input signal to at least one of the loudspeakers based on the third microphone signal and one of the first and the second microphone signal. A distance between the third position and the first position equals a distance between the third position and the second position such that the first, second and third microphones form the corners of an isosceles triangle.

A method for generating silent zones at a listening position comprises radiating with a first loudspeaker disposed at a first position adjacent to the listening position sound that corresponds to a sound signal, picking up, with a first error microphone disposed at the first position, noise radiated by a noise source via a primary path to the listening position, and generating a corresponding first microphone signal, radiating with a second loudspeaker disposed at a second position adjacent to the listening position sound that corresponds to the sound signal. The method further comprises picking up, with a second error microphone disposed at the second position, noise radiated by a noise source via a primary path to the listening position, and generating a corresponding second microphone signal. The method further comprises picking up, with a third error microphone disposed at a third position adjacent to the listening position, noise radiated by a noise source via a primary path to the listening position, and generating corresponding third microphone signals. The method further comprises providing a loudspeaker input signal to at least one of the loudspeakers based on the third microphone signal and one of the first and the second microphone signal. A distance between the third position and the first position equals a distance between the third position and the second position such that the microphones form the corners of an isosceles triangle.

Other systems, methods, features and advantages will be, or will become, apparent to one with skill in the art upon examination of the following detailed description and appended figures. It is intended that all such additional systems, methods, features and advantages be included within this description, be within the scope of the invention, and be protected by the following claims.

BRIEF DESCRIPTION OF THE DRAWINGS

The disclosure may be better understood by reading the following description of non-limiting embodiments of the attached drawings, in which like elements are referred to with like reference numbers, wherein below.

DETAILED DESCRIPTION

Figure 1:
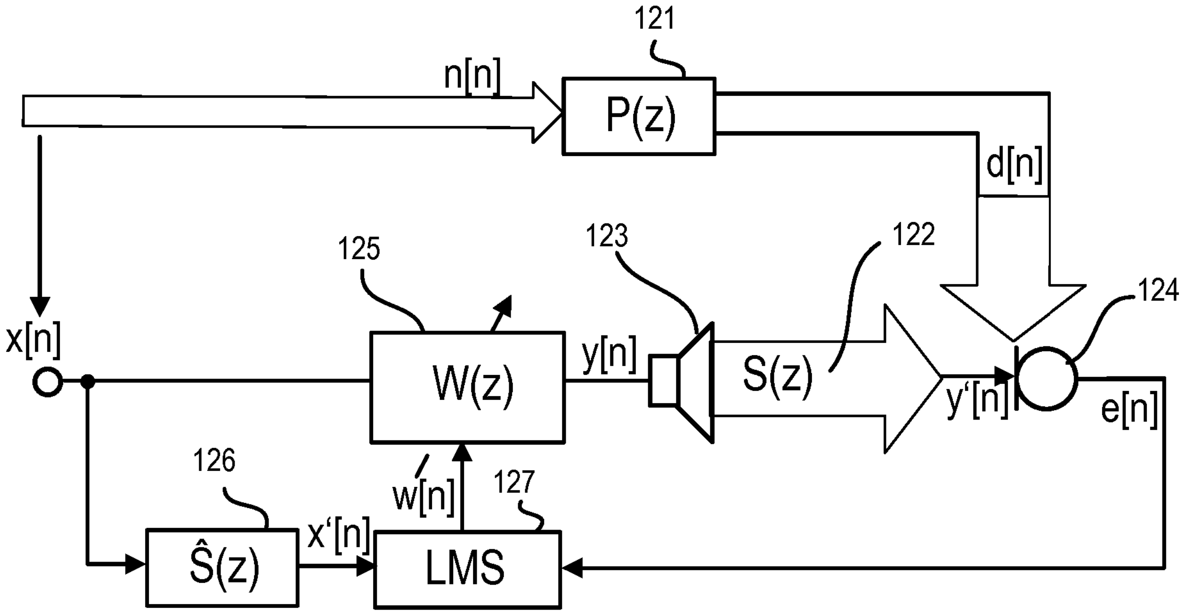
FIG. 1 is a block diagram of a general feedforward type active noise reduction system.

FIG. 1 schematically illustrates a noise reduction system, i.e. a feedforward active noise control (ANC) system. ANC systems are usually intended to reduce or even cancel a disturbing signal, such as noise, by providing at a listening site, a noise reducing signal that ideally has the same amplitude over time but the opposite phase as compared to the noise signal. By superimposing the noise signal and the noise reducing signal, the resulting signal, also known as error signal, ideally tends toward zero.

For the sake of simplicity, no distinction is made herein between electrical and acoustic signals. However, all signals provided by the loudspeaker or received by the microphone are actually of an acoustic nature. All other signals are electrical in nature. The loudspeaker and the microphone may be part of an acoustic sub-system (e.g., a loudspeaker-room-microphone system) having an input stage formed by the loudspeaker and an output stage formed by the microphone; the sub-system being supplied with an electrical input signal and providing an electrical output signal. "Path" corresponds to an electrical or acoustical connection that may include further elements such as signal conducting devices, amplifiers, filters, etc. A spectrum shaping filter is a filter in which the spectra of the input and output signals are different over frequency. Components such as, for example, amplifiers, analog-to-digital converters and digital-to-analog converters, which may be included in an actual realization of an ANC system, are not illustrated herein to further simplify the following description. All signals are denoted as digital signals with the time index n placed in squared brackets.

The ANC system in FIG. 1 uses a least mean square (LMS) algorithm and includes a primary path 121 which has a (discrete time) transfer function P(z). The transfer function P(z) represents the transfer characteristic of the signal path between a noise source, e.g., a vehicle's engine, whose noise is to be controlled and a listening position, e.g., a position in the interior of the vehicle where the noise is to be suppressed. The ANC system also includes an adaptive filter 125 with a filter transfer function W(z), and an LMS adaption unit 127 for calculating a set of filter coefficients w[n] that determines the filter transfer function W(z) of the adaptive filter 125. A secondary path 122 which has a transfer function S(z) is arranged downstream of the adaptive filter 125 and represents the signal path between a loudspeaker 123 that broadcasts a compensation signal y[n] to the listening position. For the sake of simplicity, the secondary path 122 may include the transfer characteristics of all components downstream of the adaptive filter 125, e.g., amplifiers, digital-to-analog-converters, loudspeakers, acoustic transmission paths, microphones, and analog-to-digital converters. A secondary path estimation filter 126 has a transfer function that is an estimation $\hat{S}(z)$ of the secondary path transfer function S(z). The primary path 121 and the secondary path 122 are "real" systems essentially representing the physical properties of the listening room (e.g., the vehicle cabin), wherein the other transfer functions may be implemented in a digital signal processor.

Noise n[n] generated by the noise source, which includes sound waves, accelerations, forces, vibrations, harness, etc., is transferred via the primary path 121 to the listening position where the noise n[n] appears, after being filtered with the transfer function P(z), as disturbing noise signal d[n] which represents the noise audible at the listening position, e.g., within the vehicle cabin. The noise n[n], after being picked up by a noise and vibration sensor (not illustrated) such as a force transducer sensor or an acceleration sensor, serves as a reference signal x[n]. Acceleration sensors may include accelerometers, force gauges, load cells, etc. For example, an accelerometer is a device that measures proper acceleration. Proper acceleration is not the same as coordinate acceleration, which is the rate of change of velocity. Single- and multi-axis models of accelerometers are available for detecting magnitude and direction of the proper acceleration, and can be used to sense orientation, coordinate acceleration, motion, vibration, and shock. The reference signal x[n] provided by such an acceleration sensor is input into the adaptive filter 125 which filters the reference signal x[n] with transfer function W(z) and outputs the compensation signal y[n]. The compensation signal y[n] is transferred via the secondary path 122 to the listening position where the compensation signal y[n] appears, after being filtered with the transfer function S(z), as anti-noise y'[n]. The anti-noise y'[n] and the disturbing noise d[n] are destructively superposed at the listening position. A microphone outputs a measurable residual signal, i.e. an error signal e[n] that is used for the adaption in the LMS adaption unit 127. The error signal e[n] represents the sound including (residual) noise present at the listening position, e.g., in the cabin of the vehicle.

The filter coefficients w[n] are updated based on the reference signal x[n] filtered with the estimation $\hat{S}(z)$ of the secondary path transfer function S(z) which represents the signal distortion in the secondary path 122. The secondary path estimation filter 126 is supplied with the reference signal x[n] and provides a filtered reference signal x'[n] to the LMS adaption unit 127. The overall transfer function W(z)*S(z) provided by the series connection of the adaptive filter 125 and the secondary path 122 shifts the phase of the reference signal x[n] by 180 degrees so that the disturbing noise d[n] and the anti-noise y'[n] are destructively superposed, thereby suppressing the disturbing noise d[n] at the listening position.

The error signal e[n] as measured by the microphone 124 and the filtered reference signal x'[n] provided by the secondary path estimation filter 126 are supplied to the LMS adaption unit 127. The LMS adaption unit 127 calculates the filter coefficients w[n] for the adaptive filter 125 from the filtered reference signal x'[n] ("filtered x") and the error signal e[n] such that the norm (i.e., the power or L2-Norm) of the error signal e[n] is reduced. The filter coefficients w[n] are calculated, for example, using the LMS algorithm. The adaptive filters 125, LMS adaption unit 127, and secondary path estimation filters 126 may be implemented in a digital signal processor. Of course, alternatives or modifications of the "filtered x" LMS algorithm, such as, for example, the "filtered-e" LMS algorithm, are also applicable.

An acceleration sensor may directly pick up noise n[n] in a broad frequency band of the audible spectrum. The system of FIG. 1, therefore, may be used in connection with broadband filters, wherein the broadband filter providing the transfer function W(z) may alternatively have a fixed transfer function instead of an adaptive transfer function, as the case may be. Directly picking up essentially includes picking up the signal in question with no significant influence by other signals. The exemplary system shown in FIG. 1 employs a straightforward single-channel feedforward filtered-x LMS control structure, but other control structures, e.g., multi-channel structures with a multiplicity of additional channels, a multiplicity of additional microphones, and a multiplicity of additional loudspeakers, may be applied as well. A multi-channel structure will be explained with respect to FIG. 16 further below.

When used in user-related applications, microphones of an ANC system should be positioned as close as possible to the user's head to provide superior acoustic properties. However, many environments such as, e.g., the interiors of vehicles hardly or even do not at all allow positioning of microphones close to the head. In some applications, the microphone is therefore mounted on a flexible arm, hinged holder, rigid boom, pivotable or extendable wing, or the like, extending into the direction of the user, but such arrangements are inconvenient and may bear significant risk of user injury, particularly in the case of a vehicle crash.

Figure 2:
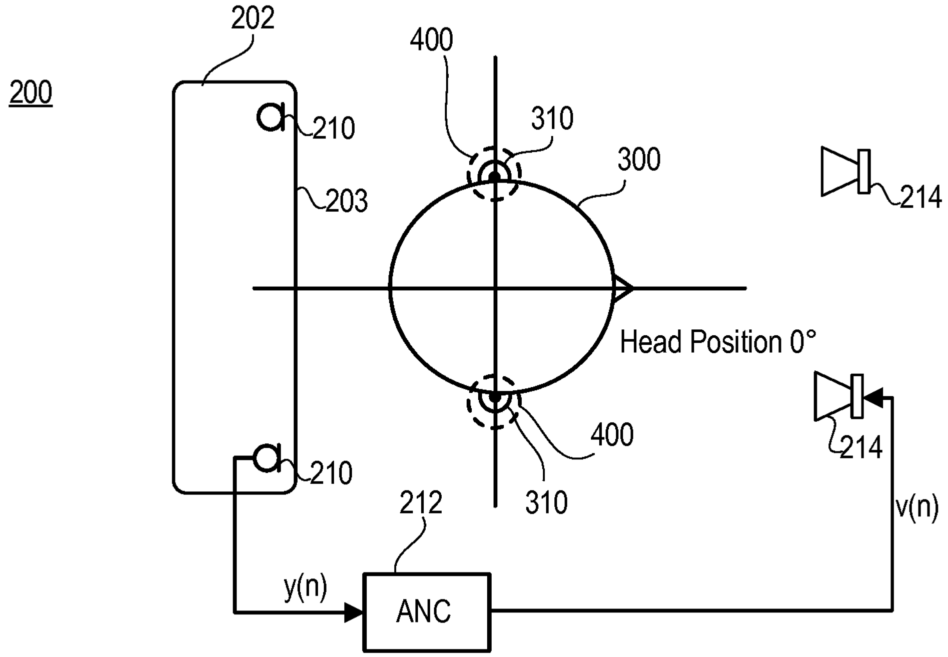
FIG. 2 is a schematic diagram of a headrest arrangement in which microphones are integrated in a front surface of a headrest with a user's head in a preferential position in front of the headrest.

FIG. 2 is a top view of a vehicle ANC system 200. A headrest 202, e.g., a headrest of a seat disposed in a vehicle interior, is illustrated in a sectional illustration. The headrest 202 may have a cover and one or more structural elements that form a headrest body. The headrest 202 may also comprise a pair of support pillars (not shown) that engage the top of a seat (not shown) and may be movable up and down by way of a mechanism integrated in the seat. The headrest 202 has a front surface 203 that is able to support a listener's head 300, thereby defining preferential positions of listener's ears 310. A preferential position of a listener's ear 310, also referred to as listening position, is an area where the respective ear 310 is most of the time (>50%) during intended use. Usually, when his ears 310 are in the preferential position, the listener 300 looks straight ahead (head position 0° with respect to an axis that is essentially perpendicular to the front surface 203 of the headrest 202).

Microphones 210 are integrated in the headrest 202 and their directions of maximum sensitivity may intersect with the preferential positions of the listener's ears 310. Around the preferential positions of the listener's ears 310, respectively, silent zones 400 (areas with less or no noise) are to be established. The system further includes loudspeakers 214 arranged in front of the listener 300, e.g., in a dashboard of the vehicle. The loudspeakers 214 may each have principal transmitting directions into which they radiate maximum sound pressure, e.g., in the direction of the listener's head 300.

The system 200 further comprises an ANC controller 212 having a noise control structure that may be feedforward or feedback (see FIG. 1) or a combination thereof. The ANC controller 212 receives a microphone output signal y(n) from at least one of the microphones 210 in the headrest 202. The ANC controller 212 is configured, based on at least one of the microphone output signals y(n), to provide a loudspeaker input signal v(n) to at least one of the loudspeakers 214.

Figure 3:
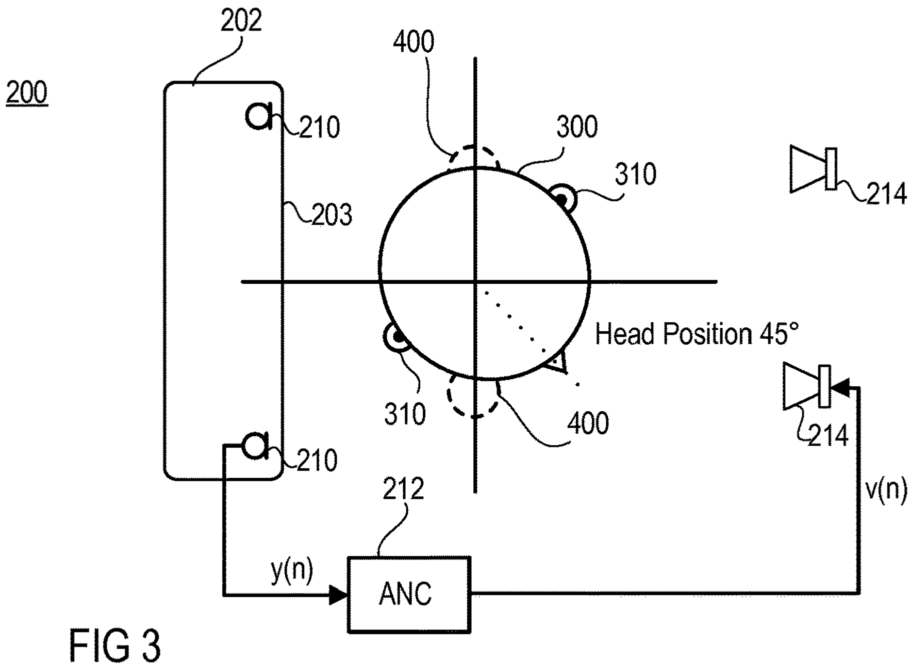
FIG. 3 illustrates the headrest arrangement of FIG. 2 with the user's head having a deviation from the preferential position.

The silent zones 400 that are generated by the system 200 of FIG. 2 are generally rather small. While in the preferential position, the listener's ears 310 are usually at least partly arranged within the silent zones 400. However, as is illustrated in FIG. 3, if the listener 300 moves his head to one side, for example, the ears 310 move out of the silent zones 400, as the silent zones 400 remain unaffected by the movement of the listener's head 300. In the example that is illustrated in FIG. 3, the user 300 turns his head about 45° with respect to the axis that is essentially perpendicular to the front surface 203 of the headrest 202. Noise cancellation is experienced as less satisfactory if the listener 300 moves his ears 310 out of the silent zones 400.

Figure 4:
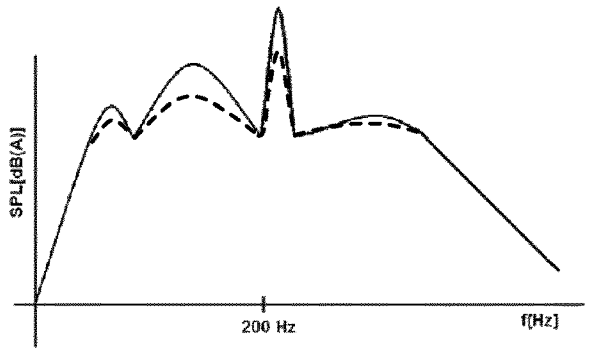
FIG. 4, in a diagram, illustrates the resulting sound pressure level for different frequencies for the headrest arrangement shown in FIGS. 2 and 3.
Figure 5:
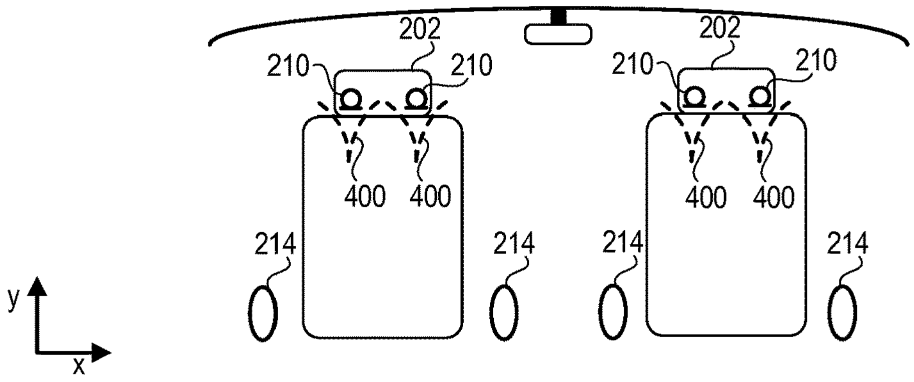
FIG. 5 illustrates in a frontal view the headrest arrangement of FIGS. 2 and 3 and the resulting shape of the silent zone.

FIG. 4 exemplarily illustrates the sound pressure level in the silent zones 400 of the system of FIGS. 2 and 3. The solid line illustrates the sound pressure level if active noise cancellation is not active, while the dashed line illustrates the sound pressure level if active noise cancellation is active. As can be seen, the sound pressure level can be reduced a good amount for a quite large frequency range. Only for very low frequencies as well as for higher frequencies results are poor. The silent zones 400 generated by the system of FIGS. 2 and 3, however, are comparably small. That is, small movements of the listener's head already result in the ears 310 being located outside the silent zones 400. FIG. 5 exemplarily illustrates a frontal view of the system of FIGS. 2 and 3. The dashed lines serve to schematically illustrate the silent zones 400. As can be seen, the silent zones are comparably narrow in a first horizontal direction x.

Figure 6:
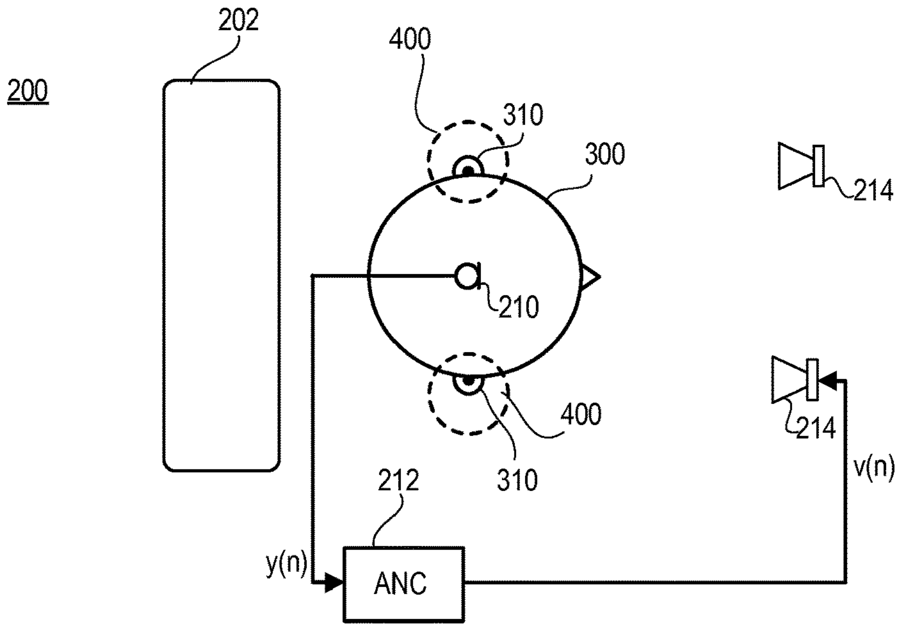
FIG. 6 is a schematic diagram of a headrest arrangement in which a microphone is arranged above a user's head in front of the headrest.
Figure 7:
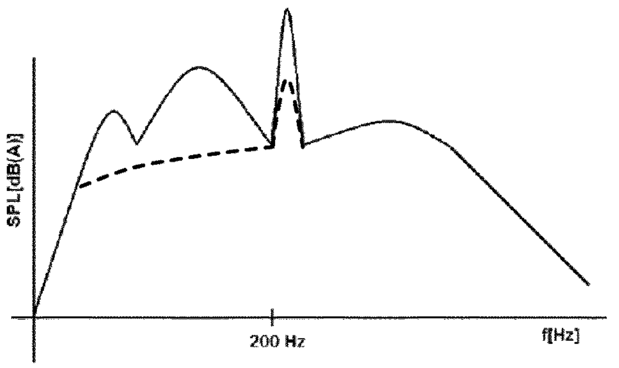
FIG. 7, in a diagram, illustrates the resulting sound pressure level for different frequencies for the headrest arrangement shown in FIG. 6.
Figure 8:
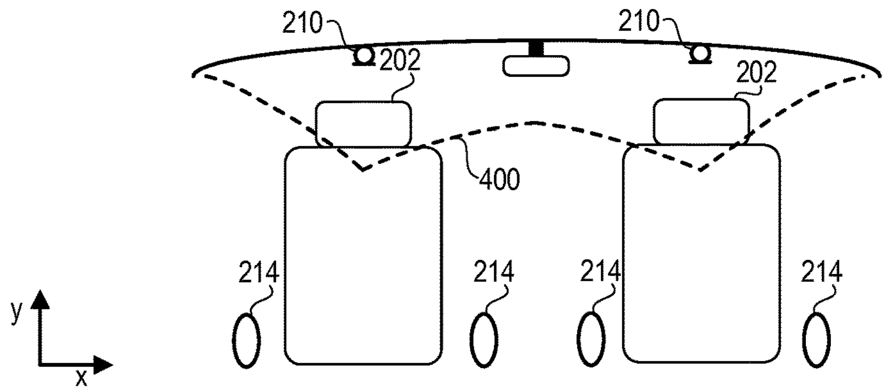
FIG. 8 illustrates in a frontal view the headrest arrangement of FIG. 6 and the resulting shape of the silent zone.

FIG. 6 schematically illustrates another system. In the system of FIG. 6, one microphone 210 is arranged above the listener's head 300 in front of the headrest 202. For example, the microphone 210 may be arranged in the roof liner of the vehicle above the user's head 300. The loudspeakers 214 are arranged in front of the listener 300, as in the system of FIGS. 2 and 3. As is indicated in FIG. 6 and as can be seen from the frontal view of the system in FIG. 8, the silent zones 400 are larger as compared to the silent zones 400 of the system of FIGS. 2 and 3. However, as can be seen in the diagram illustrated in FIG. 7, the results of the noise cancellation are rather poor for frequencies above about 200 Hz. That is, even if the silent zones 400 are larger, the noise cancellation only provides satisfactory results in a limited frequency range of about 20-200 Hz. The solid line again illustrates the sound pressure level if active noise cancellation is not active, while the dashed line illustrates the sound pressure level if active noise cancellation is active.

Figure 9:
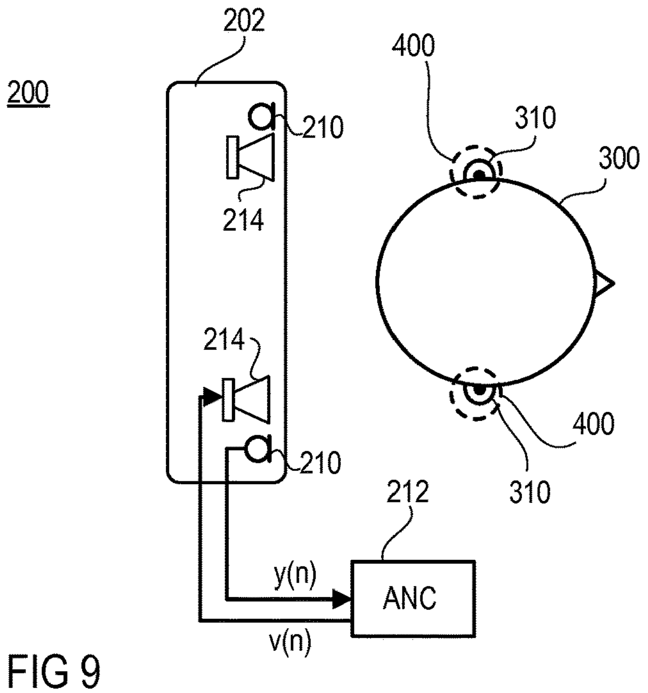
FIG. 9 is a schematic diagram of a headrest arrangement in which microphones and loudspeakers are arranged in a front surface of a headrest.
Figure 10:
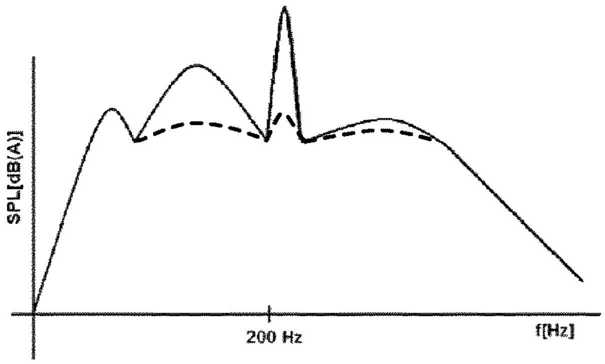
FIG. 10, in a diagram, illustrates the resulting sound pressure level for different frequencies for the headrest arrangement shown in FIG. 9.
Figure 11:
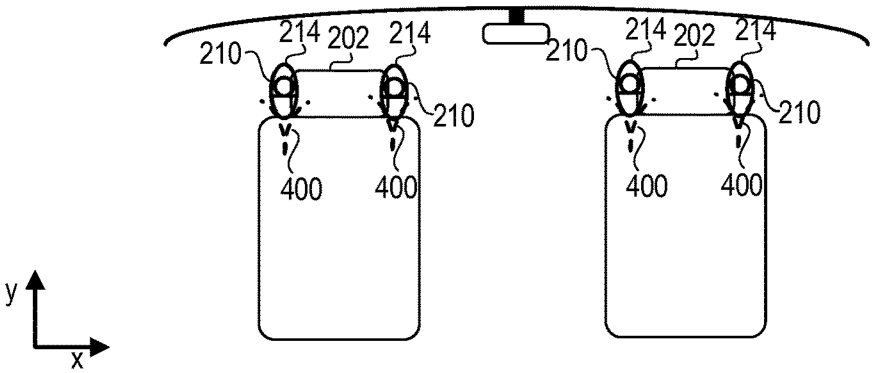
FIG. 11 illustrates in a frontal view the headrest arrangement of FIG. 9 and the resulting shape of the silent zone.

FIG. 9 schematically illustrates another system. In the system of FIG. 9, the microphones 210 and the loudspeakers 214 are arranged in the headrest 202. As is indicated in FIG. 9 and as can be seen from the frontal view of the system in FIG. 11, the silent zones 400 are rather narrow, similar to the system of FIGS. 2 and 3. As can be seen in the diagram in FIG. 10, the results of noise cancellation are acceptable for a comparably broad frequency range. The solid line again illustrates the sound pressure level if active noise cancellation is not active, while the dashed line illustrates the sound pressure level if active noise cancellation is active.

In the systems of FIGS. 2, 6 and 9, maximum noise cancellation is achieved at the positions of the microphones 210. As the ears 310 of the listener 300 are arranged at a certain distance from the microphones 210, noise cancellation at the ears is generally less satisfactory. However, this is usually accepted in favor of the microphones not being arranged in direct vicinity of the ears 310, as has already been outlined above.

Figure 12:
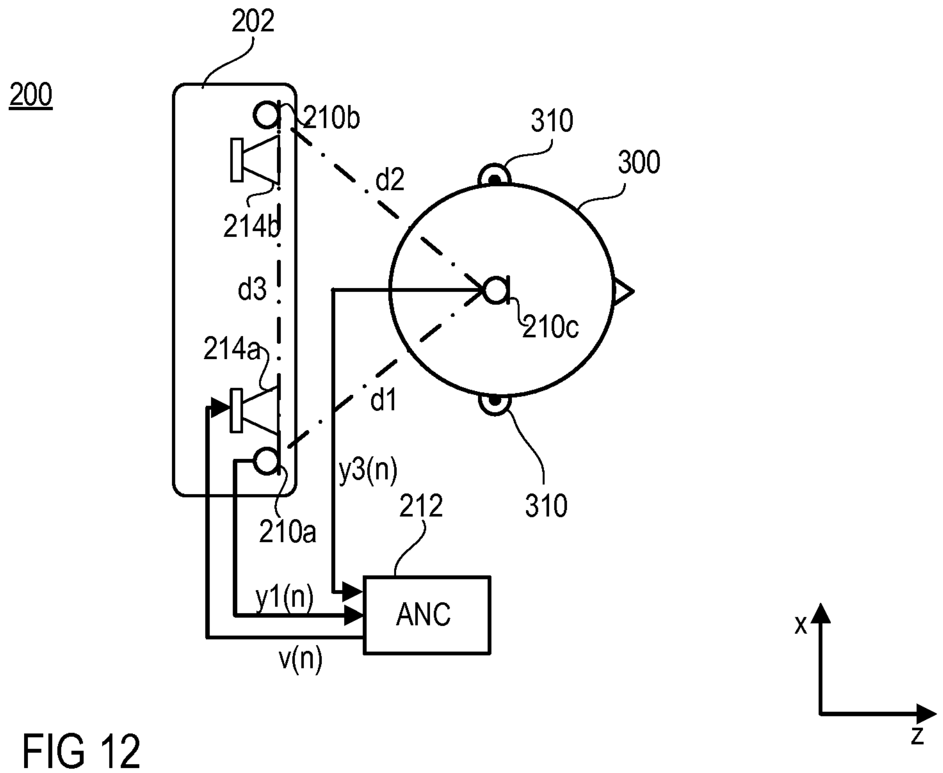
FIG. 12 is a schematic diagram of an exemplary headrest arrangement in which microphones and loudspeakers are arranged in a front surface of a headrest and an additional microphone is arranged above a user's head in front of the headrest.
Figure 13:
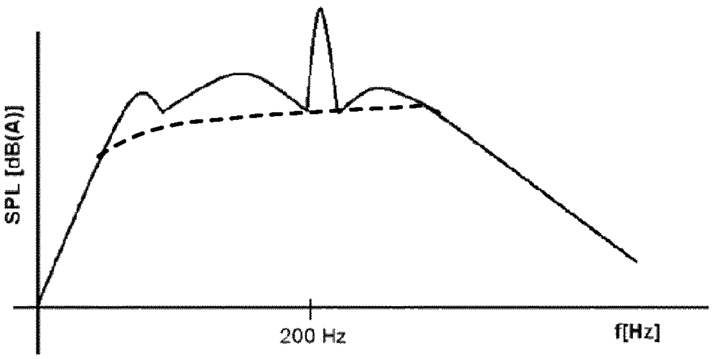
FIG. 13, in a diagram, illustrates the resulting sound pressure level for different frequencies for the headrest arrangement shown in FIG. 12.

FIG. 12 schematically illustrates an exemplary embodiment. A first microphone 210*a* is arranged at a first position in the headrest 202. A first loudspeaker 214*a* is also arranged at the first position in the headrest 202. In FIG. 12, the first microphone 210*a* and first loudspeaker 214*a* are illustrated with a small distance in between. However, as the microphone 210*a* is usually small as compared to the loudspeaker 214*a*, the microphone 210*a* may be placed in front of the loudspeaker 214*a*, for example, such that the first microphone 210*a* and the first loudspeaker 214*a* can effectively be seen as being placed at the same position. It is also possible that the first microphone 210*a* and the first loudspeaker 214*a* are arranged adjacent to each other with only a small or no distance (e.g., distance<1 cm) in between which can also effectively be seen as the same position.

The same applies to the second microphone 210*b* and the second loudspeaker 214*b* that are arranged at a second position in the headrest 202. The second position, however, is distant to the first position. For example, a distance d3 between the first position and the second position in a first horizontal direction x may be 10 cm or more. A third error microphone 210*c* is arranged above the listener's head 300 in front of the headrest 202, e.g., in a roof liner of a vehicle interior. In front of the headrest 202 within this context indicates that the third microphone 210*c* is not arranged directly above the headrest 202 but is arranged offset to the first and second positions in a second horizontal direction z, wherein the second horizontal direction z is perpendicular to the first horizontal direction x.

The third error microphone 210*c* measures and feeds back background noise occurring around the headrest 202. Signals output by the third feedback microphone 210*c*, herein referred to as third error signals y3(n), are combined with one or more sound signals supplied to the first loudspeaker 214*a* and one or more first error signals y1(n) from the first error microphone 210*a* embedded in the headrest 202 to create a first silent zone 400 about a first ear 310 of the listener 300 (e.g., right ear). The third error signals y3(n) may further be combined with one or more sound signals supplied to the second loudspeaker 214*b* and one or more second error signals y2(z) from the second error microphone 210*b* embedded in the headrest 202 in order to create a second silent zone 400 about a second ear 310 of the listener 300 (e.g., left ear). An ANC controller 212 is exemplarily illustrated which provides a first loudspeaker input signal v(n) to be output by the first loudspeaker 214*a*. The ANC controller 212, although not illustrated, may also provide a second loudspeaker input signal to be output to the second loudspeaker 214*b*. A second loudspeaker input signal for the second loudspeaker 214*b*, however, may also be provided by a separate second ANC controller (not illustrated).

Figure 14:
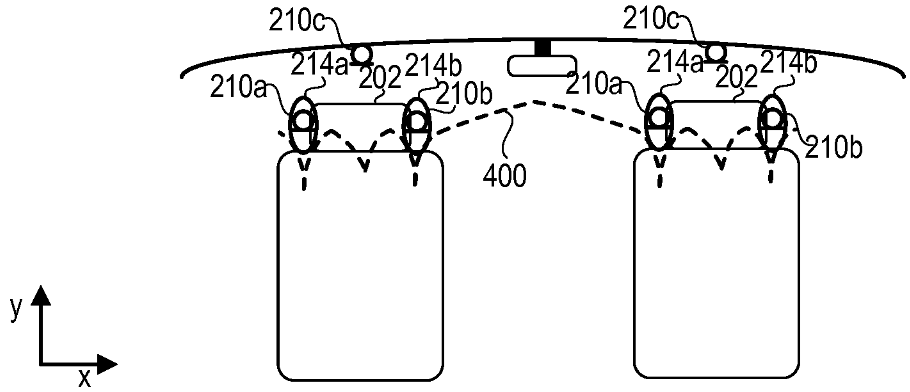
FIG. 14 illustrates in a frontal view the headrest arrangement of FIG. 12 and the resulting shape of the silent zone.
Figure 15:
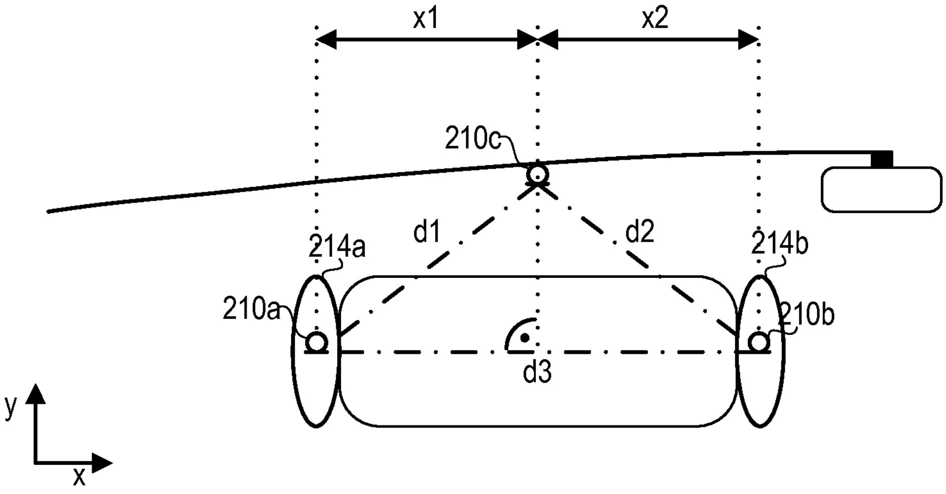
FIG. 15 illustrates the arrangement of the loudspeakers and microphones of the headrest arrangement of FIG. 12 in greater detail.

As can be seen from the frontal view of the system illustrated in FIG. 14, the third error microphone 210*c* is further arranged offset to the first and second positions in a vertical direction y which is perpendicular to the first and the second horizontal directions x, z. The first, second and third microphones 210*a*, 210*b*, 210*c* form the corners of an isosceles triangle. This is schematically illustrated in FIG. 15, which illustrates a section of the front view of FIG. 14 in further detail. In particular, FIG. 15 illustrates a microphone arrangement for one of the passengers of a vehicle, e.g., the driver. The distance d3 between the first and the second position forms the base of the triangle and the distances d1, d2 between the third microphone 210*c* and the first position and the third microphone and the second position form the legs of the triangle, wherein the legs are equally long, that is d1=d2. In the first horizontal direction x, the third microphone 210*c* is arranged halfway between the first position and the second position, that is, x1=x2, wherein x1+x2=d3 (see FIG. 15).

Figure 16:
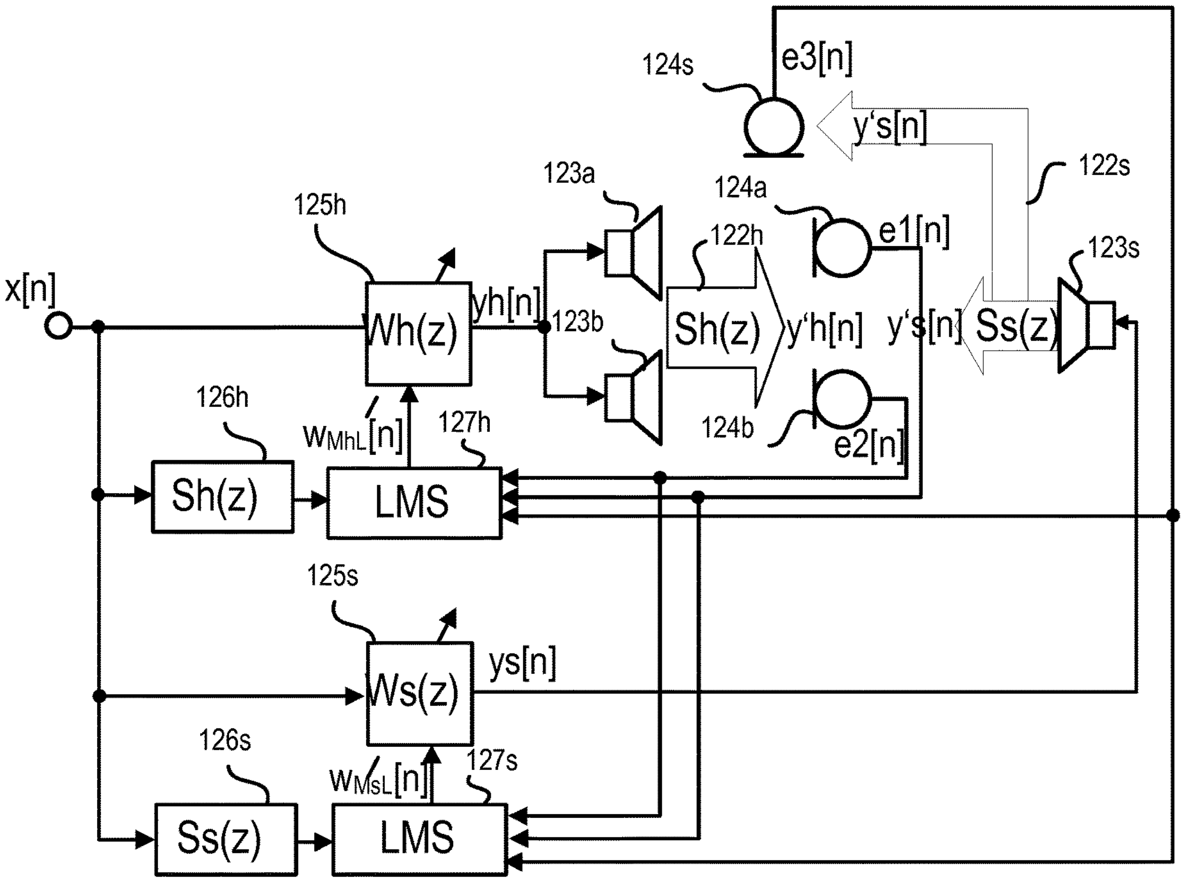
FIG. 16 is a block diagram of an exemplary feedforward type active noise reduction system.

Now referring to FIG. 16, a block diagram of an exemplary multi-channel feedforward type active noise reduction system is illustrated. The noise reduction system of FIG. 16 generally corresponds to the single-channel noise reduction system that has been described with respect to FIG. 1 above. The primary path is not specifically illustrated in FIG. 16. The ANC system in FIG. 16 includes a first and a second loudspeaker 123*a*, 123*b*. The first and second loudspeakers 123*a*, 123*b* correspond to the loudspeakers 214 arranged in the headrest, as described with respect to FIGS. 12 to 15 above. The ANC system of FIG. 16 further comprises at least one third loudspeaker 123*s*, which corresponds to a loudspeaker of, e.g., a sound system that may be arranged in front of the listener, e.g., in a dashboard of the vehicle. In FIG. 16 only one third loudspeaker 123*s* is schematically illustrated. According to one example, however, the system may comprise more than one, e.g., five third loudspeakers 123*s*. The active noise reduction system further comprises three feedback microphones 124*a*, 124*b*, 124*c*. The feedback microphones 124*a*, 124*b*, 124*c* correspond to the first microphone 210*a*, the second microphone 210*b*, and the third microphone 210*c* of FIGS. 12 to 15, for example, for generating a silent zone 400 for an ear 310 of the user 300. That is, the microphones 124*a*, 124*b* may be arranged in a headrest of the vehicle and the microphone 124*c* may be arranged above the listener's head 300 in front of the headrest 202, e.g., in a roof liner of a vehicle interior.

A first secondary path matrix which has a first transfer function Sh(z) is arranged downstream of a first adaptive filter 125*h* and represents the signal path between a headrest loudspeaker 123*a*, 123*b* that broadcasts a first compensation signal yh[n] to each of the headrest loudspeakers 123*a*, 123*b*. Secondary path matrix in this context refers to all possible combinations from each of the multiple headrest loudspeakers 123*a*, 123*b* to each of the multiple microphones 124*a*, 124*b*, 124*c*. In the example of FIG. 16, the first secondary path matrix may be a 2×2 matrix (2 loudspeakers, 2 microphones). A second secondary path matrix which has a second transfer function Ss(z) is arranged downstream of a second adaptive filter 125*s* and represents the signal path between one or more loudspeakers 123*s* of a sound system arranged in front of the listener that broadcast a second compensation signal ys[n] to each of the microphones 124*a*, 124*b*, 124*c*. Secondary path matrix in this context refers to all possible combinations from the loudspeakers 123*s* to each of the multiple microphones 124*a*, 124*b*, 124*c*. In the example of FIG. 16, the second secondary path matrix may be a K×5 matrix (K microphones, 5 sound system loudspeakers). The secondary path estimation filters 126*h*, 126*s* are similar to the secondary path estimation filter 126 that has been described with respect to FIG. 1. Each of the microphones 124 delivers an error signal e1[n], e2[n], e3[n]. The error signals e1[n], e2[n], e3[n] are received by two LMS adaption units 127*h*, 127*s*. The function of the LMS adaption units 127*h*, 127*s* is similar to the function of the LMS adaption unit 127 that has been described with respect to FIG. 1 above. Each LMS adaption unit 127*h*, 127*s* may use all three error signals e1[n], e2[n], e3[n] for the adaption.

The least mean square (LMS) algorithm of the system shown in FIG. 16 is splitted into two adaptive equations, one for the headrest loudspeakers 123*a*, 123*b* (Mh: number of headrest speakers) and one for the car audio system speakers ($M_s$: number of sound system speakers).

The equation for headrest processing can be described as follows:

$$w_{M_hL}(n+1)=w_{M_hL}(n)+\mu_{M_hL}\Sigma_{m=1}^{M_h}ifft(R_{LM_hK}E_{L_h}) \quad (1)$$

where L is the number of headrest microphones, K is the number of reference signals x[n], $\mu_{MhL}$ is the step size for the headrest speakers, $R_{LMhK}$ is the cross-spectra matrix of the filtered reference signals, and $E_{Lh}$ are the headrest microphones for each seat plus the closest headliner microphone that they form a triangle with. In the equation, ifft refers to the inverse fast fourier transformation. Therefore, this equation applies for creating individual zones of silence in the vehicle environment.

The equation for the system loudspeaker processing $E_{Ls}$ can be described as follows:

$$w_{M_sL}(n+1)=w_{M_sL}(n)+\mu_{M_sL}\Sigma_{m=1}^{M_h}ifft(R_{LM_sL}E_L) \quad (2)$$

where L is the number of microphones, K is the number of reference signals x[n], $\mu_{MsL}$ is the step size for the headliner speaker, $R_{LMsL}$ is the cross-spectra matrix of the filtered reference signals, and $E_L$ are the error signals of all microphones (headliner and headrest mounted microphones).

The adaptive filters 125*h*, 125*s*, the LMS adaption units 127*h*, 127*s*, and the secondary path estimation filters 126*h*, 126*s* may be included in the ANC controller 212 of FIG. 12, for example.

The systems and methods described herein may be used in a multiplicity of applications and environments such as, for example, in living areas and in interiors of vehicles to generate dedicated silent or sound zones. Beside general noise control, the system and methods described herein are also applicable in specific control situations such as road noise control in land-based vehicles or engine order cancellation in combustion engine driven vehicles.

The description of embodiments has been presented for purposes of illustration and description. Suitable modifications and variations to the embodiments may be performed in light of the above description or may be acquired by practicing the methods. For example, unless otherwise noted, one or more of the described methods may be performed by a suitable device and/or combination of devices. The described associated actions may also be performed in various orders in addition to the order described in this application, in parallel, and/or simultaneously. The described systems are exemplary in nature, and may include additional elements and/or omit elements.

As used in this application, an element or step recited in the singular and preceded by the word "a" or "an" should be understood as not excluding the plural of said elements or steps, unless such exclusion is stated. Furthermore, references to "one embodiment" or "one example" of the present disclosure are not intended to be interpreted as excluding the existence of additional embodiments that also incorporate the recited features. The terms "first," "second," and "third," etc. are used merely as labels, and are not intended to impose numerical requirements or a particular positional order on their objects.

The embodiments of the present disclosure generally provide for a plurality of circuits, electrical devices, and/or at least one controller. All references to the circuits, the at least one controller, and other electrical devices and the functionality provided by each, are not intended to be limited to encompassing only what is illustrated and described herein. While particular labels may be assigned to the various circuit(s), controller(s) and other electrical devices disclosed, such labels are not intended to limit the scope of operation for the various circuit(s), controller(s) and other electrical devices. Such circuit(s), controller(s) and other electrical devices may be combined with each other and/or separated in any manner based on the particular type of electrical implementation that is desired.

It is recognized that any system as disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any system as disclosed may utilize any one or more microprocessors to execute a computer-program that is embodied in a non-transitory computer readable medium that is programmed to perform any number of the functions as disclosed. Further, any controller as provided herein includes a housing and a various number of microprocessors, integrated circuits, and memory devices, (e.g., FLASH, random access memory (RAM), read only memory (ROM), electrically programmable read only memory (EPROM), and/or electrically erasable programmable read only memory (EEPROM).

While various embodiments of the invention have been described, it will be apparent to those of ordinary skilled in the art that many more embodiments and implementations are possible within the scope of the invention. In particular, the skilled person will recognize the interchangeability of various features from different embodiments. Although these techniques and systems have been disclosed in the context of certain embodiments and examples, it will be understood that these techniques and systems may be extended beyond the specifically disclosed embodiments to other embodiments and/or uses and obvious modifications thereof.

The invention claimed is:

1. A system for generating silent zones at a listening position, the system comprising:

a first loudspeaker disposed at a first position adjacent to the listening position and configured to radiate sound that corresponds to a sound signal;

a first microphone disposed at the first position and configured to pick up noise radiated by a noise source via a primary path to the listening position, and configured to generate a corresponding first microphone signal;

a second loudspeaker disposed at a second position adjacent to the listening position and configured to radiate sound that corresponds to a sound signal;

a second microphone disposed at the second position and configured to pick up the noise radiated by the noise source via the primary path to the listening position and configured to generate a corresponding second microphone signal;

a third microphone disposed at a third position adjacent to the listening position and configured to pick up the noise radiated by the noise source via the primary path to the listening position and configured to generate a corresponding third microphone signal; and an active noise cancellation (ANC) controller configured to receive the third microphone signal from the third microphone and at least one of the first and second microphone signals from at least one of the first and second microphone, respectively, and to provide a loudspeaker input signal to at least one of the first and second loudspeakers based on the third microphone signal and the at least one of the first and the second microphone signals, wherein a distance between the third position and the first position equals a distance between the third position and the second position such that the first, second and third microphones form corners of an isosceles triangle.

2. The system of claim 1, wherein:

the first microphone and the first loudspeaker are arranged in a headrest of a vehicle; and the second microphone and the second loudspeaker are arranged in the headrest, distant to the first microphone and the first loudspeaker.

3. The system of claim 1, wherein the third microphone is arranged offset to the first position in a first horizontal direction, in a second horizontal direction perpendicular to the first horizontal direction, and in a vertical direction perpendicular to the first and the second horizontal direction; and the third microphone is arranged offset to the second position in the first horizontal direction, in the second horizontal direction, and in the vertical direction.

4. The system of claim 1, wherein the ANC controller comprises a first adaptive filter that is coupled to the first and second loudspeakers.

5. The system of claim 4, wherein the ANC controller further comprises a first least mean square (LMS) adaption unit for calculating a set of filter coefficients that determines a filter transfer function of the first adaptive filter based on the first, second and third microphone signals.

6. The system of claim 5, further comprising a secondary path arranged downstream of the first adaptive filter and having a secondary path transfer function, wherein the filter coefficients are updated based on a reference signal filtered with an estimation of the secondary path transfer function which represents a signal distortion in the secondary path.

7. The system of claim 5, wherein the ANC controller further comprises at least one third loudspeaker, a second adaptive filter that is coupled to the at least one third loudspeaker, and a second LMS adaption unit for calculating a set of second filter coefficients that determines a filter transfer function of the second adaptive filter based on the first, second, and third microphone signals.

8. The system of claim 7, further comprising a secondary path arranged downstream of the second adaptive filter and having a secondary path transfer function, wherein the second filter coefficients are updated based on a reference signal filtered with an estimation of the second secondary path transfer function which represents a signal distortion in the secondary path.

9. A method for generating silent zones at a listening position, the method comprising:

radiating with a first loudspeaker disposed at a first position adjacent to the listening position sound that corresponds to a sound signal;

picking up with a first microphone disposed at the first position, noise radiated by a noise source via a primary path to the listening position, and generating a corresponding first microphone signal;

radiating with a second loudspeaker disposed at a second position adjacent to the listening position sound that corresponds to the sound signal;

picking up with a second microphone disposed at the second position, the noise radiated by the noise source via the primary path to the listening position, and generating a corresponding second microphone signal;

picking up with a third microphone disposed at a third position adjacent to the listening position, the noise radiated by the noise source via the primary path to the listening position, and generating a corresponding third microphone signal; and providing a loudspeaker input signal to at least one of the first and second loudspeakers based on the third microphone signal and one of the first and the second microphone signals, wherein a distance between the third position and the first position equals a distance between the third position and the second position such that the first, second, and third microphones form corners of an isosceles triangle.

10. The method of claim 9, further comprising filtering, with a first adaptive filter, a reference signal with an estimation of a secondary path transfer function which represents a signal distortion in a secondary path that is arranged downstream of the first adaptive filter.

11. The method of claim 10, further comprising calculating a set of filter coefficients that determines a filter transfer function of the first adaptive filter based on the first, second, and third microphone signals.

12. The method of claim 10 further comprising filtering, with a second adaptive filter, the reference signal with an estimation of a secondary path transfer function which represents a signal distortion in a secondary path arranged downstream of the second adaptive filter.

13. The method of claim 12 further comprising calculating a set of filter coefficients that determines a filter transfer function of the second adaptive filter based on the first, second, and third microphone signal.

14. A system for generating silent zones at a listening position, the system comprising:

a first loudspeaker disposed at a first position about the listening position and configured to radiate sound that corresponds to a sound signal;

a first microphone disposed at the first position and configured to pick up noise radiated by a noise source to the listening position, and configured to generate a corresponding first microphone signal;

a second loudspeaker disposed at a second position adjacent to the listening position and configured to radiate sound that corresponds to a sound signal;

a second microphone disposed at the second position and configured to pick up the noise radiated by the noise source to the listening position and configured to generate a corresponding second microphone signal;

a third microphone disposed at a third position about the listening position and configured to pick up the noise radiated by the noise source to the listening position and configured to generate a corresponding third microphone signal; and an active noise cancellation (ANC) controller configured to receive the third microphone signal from the third microphone and at least one of the first and second microphone signals from at least one of the first and second microphone, respectively, and to provide a loudspeaker input signal to at least one of the first and second loudspeakers based on the third microphone signal and the at least one of the first and the second microphone signals, wherein a distance between the third position and the first position equals a distance between the third position and the second position such that the first, second and third microphones form corners of an isosceles triangle.

15. The system of claim 14, wherein:

the first microphone and the first loudspeaker are arranged in a headrest of a vehicle; and the second microphone and the second loudspeaker are arranged in the headrest, distant to the first microphone and the first loudspeaker.

16. The system of claim 14, wherein the third microphone is arranged offset to the first position in a first horizontal direction, in a second horizontal direction perpendicular to the first horizontal direction, and in a vertical direction perpendicular to the first and the second horizontal direction; and the third microphone is arranged offset to the second position in the first horizontal direction, in the second horizontal direction, and in the vertical direction.

17. The system of claim 14, wherein the ANC controller comprises a first adaptive filter that is coupled to the first and second loudspeakers.

18. The system of claim 17, wherein the ANC controller further comprises a first least mean square (LMS) adaption unit for calculating a set of filter coefficients that determines a filter transfer function of the first adaptive filter based on the first, second and third microphone signals.

19. The system of claim 18, further comprising a secondary path arranged downstream of the first adaptive filter and having a secondary path transfer function, wherein the filter coefficients are updated based on a reference signal filtered with an estimation of the secondary path transfer function which represents a signal distortion in the secondary path.

20. The system of claim 18, wherein the ANC controller further comprises at least one third loudspeaker, a second adaptive filter that is coupled to the at least one third loudspeaker, and a second LMS adaption unit for calculating a set of second filter coefficients that determines a filter transfer function of the second adaptive filter based on the first, second, and third microphone signals.

21. The system of claim 1, wherein the first loudspeaker is positioned at a same location of the first microphone, the second microphone, and the third microphone, respectively.

22. The system of claim 1, wherein the second loudspeaker is positioned at a same location of the second microphone.

23. The system of claim 1, wherein the third loudspeaker is positioned at a same location of the third microphone.

* * * * *